(12) United States Patent
Holzner et al.

(10) Patent No.: US 8,021,154 B2
(45) Date of Patent: Sep. 20, 2011

(54) METHOD FOR MANUFACTURING DENTAL PROSTHESES, METHOD FOR CREATING A DATA RECORD AND COMPUTER-READABLE MEDIUM

(75) Inventors: Stephan Holzner, Hohenschaftlarn (DE); Gerhard Weber, Purgen (DE)

(73) Assignee: Straumann Holding AG, Basel (CH)

( * ) Notice: Subject to any disclaimer, the term of this patent is extended or adjusted under 35 U.S.C. 154(b) by 523 days.

(21) Appl. No.: 12/056,863

(22) Filed: Mar. 27, 2008

(65) Prior Publication Data

US 2008/0241798 A1 Oct. 2, 2008

(30) Foreign Application Priority Data

Mar. 28, 2007 (DE) .................. 10 2007 014 985

(51) Int. Cl.
*A61C 5/10* (2006.01)
*A61C 13/08* (2006.01)
*G06F 19/00* (2006.01)

(52) U.S. Cl. ....... 433/223; 433/202.1; 700/98; 700/118; 700/187; 700/190

(58) Field of Classification Search .................... 700/98, 700/118, 163, 95, 97, 108, 109, 117, 159, 700/186, 187, 190, 191; 433/49, 195, 212.1, 433/215, 218, 223, 202.1, 219, 229; 264/16–19; 407/53, 54
See application file for complete search history.

(56) References Cited

U.S. PATENT DOCUMENTS

| | | | | |
|---|---|---|---|---|
| 4,300,862 A | * | 11/1981 | Yada | 407/53 |
| 5,289,383 A | * | 2/1994 | Sawamura et al. | 700/187 |
| 5,378,154 A | * | 1/1995 | Van Der Zel | 433/223 |
| 5,545,039 A | * | 8/1996 | Mushabac | 433/215 |
| 5,997,681 A | | 12/1999 | Kinzie | |
| 6,102,697 A | * | 8/2000 | Cicchetti | 433/49 |
| 6,766,217 B1 | * | 7/2004 | Hamada | 700/163 |
| 6,772,026 B2 | * | 8/2004 | Bradbury et al. | 700/98 |
| 6,979,496 B2 | | 12/2005 | Haymann et al. | |
| 7,153,135 B1 | | 12/2006 | Thomas | |
| 7,403,830 B2 | * | 7/2008 | Weber et al. | 700/98 |
| 7,536,234 B2 | * | 5/2009 | Kopelman et al. | 700/118 |

(Continued)

FOREIGN PATENT DOCUMENTS

DE 10 2004 052 365 A1 5/2006

(Continued)

OTHER PUBLICATIONS

European Search Report corresponding to European Application 08005998.3-2318.

(Continued)

*Primary Examiner* — Crystal J Barnes-Bullock
(74) *Attorney, Agent, or Firm* — Rissman Hendricks & Oliverio, LLP

(57) ABSTRACT

A method for manufacturing one or several dental prostheses, comprising the steps of: performing a rapid prototyping method for manufacturing one or several dental prostheses and subsequent working, such as reworking, of the one or several dental prostheses with a machining method, such as a milling method. In addition, a method for creating a data record which can be used for a rapid prototyping method for manufacturing a dental prosthesis wherein an end data record is obtained from a starting data record, so that in at least one area of a dental prosthesis manufactured with the end data record excess material is provided, compared to a dental prosthesis manufactured with the starting data record.

8 Claims, 6 Drawing Sheets

U.S. PATENT DOCUMENTS

| | | | |
|---|---|---|---|
| 7,689,308 B2 * | 3/2010 | Holzner et al. | 700/97 |
| 7,690,920 B2 * | 4/2010 | Hunt et al. | 433/218 |
| 2002/0187458 A1 * | 12/2002 | Dolabdjian et al. | 433/218 |
| 2004/0167646 A1 | 8/2004 | Jelonek et al. | |
| 2006/0063135 A1 * | 3/2006 | Mehl | 433/223 |
| 2006/0172263 A1 * | 8/2006 | Quadling et al. | 433/229 |
| 2007/0071631 A1 | 3/2007 | Laschutza et al. | |
| 2007/0292821 A1 * | 12/2007 | De Vreese | 433/195 |
| 2008/0050700 A1 * | 2/2008 | Weber et al. | 433/202.1 |
| 2008/0230397 A1 | 9/2008 | Fecher et al. | |
| 2008/0306620 A1 * | 12/2008 | Mutscheller | 700/109 |
| 2009/0026643 A1 * | 1/2009 | Wiest et al. | 264/16 |
| 2009/0186319 A1 * | 7/2009 | Sager | 433/223 |
| 2009/0319068 A1 * | 12/2009 | Sager | 700/98 |
| 2010/0203478 A1 * | 8/2010 | Rubbert | 433/212.1 |

FOREIGN PATENT DOCUMENTS

| | | |
|---|---|---|
| DE | 10 2005 038 074 A1 | 2/2007 |
| DE | 102007013638 A | 2/2008 |
| EP | 1759682 A | 3/2007 |
| WO | WO 2007/005490 A | 1/2007 |

OTHER PUBLICATIONS

Jul. 21, 2009 German Office Action in corresponding German Application No. 1020070149850.

German Patent Office Communication of Apr. 14, 2011 in corresponding DE Patent Application 10 2007 014 985.0-43, Partial English summary.

* cited by examiner

METHOD FOR MANUFACTURING DENTAL PROSTHESES, METHOD FOR CREATING A DATA RECORD AND COMPUTER-READABLE MEDIUM

FIELD OF THE INVENTION

The invention relates to a method for manufacturing dental prostheses, a method for creating a data record as well as a computer-readable medium.

BACKGROUND

It is known from the prior art to manufacture dental prostheses for example by laser sintering. In the process, for example a metal powder is locally melted so that it solidifies upon cooling in the molten area. In this manner, a three-dimensional dental prosthesis can be manufactured by applying powder in layers and subsequently selectively sintering the same. A disadvantage of this method is that normally step-like or very rough surfaces result from the application of material in layers and subsequent local sintering. The precision desired for dental prostheses can often not be achieved.

It is furthermore known from the prior art to mill dental prostheses out of solid material. By this method, dental prostheses of sufficiently high precision can be made. In this process, however, material consumption can be considerable, so that the manufacture is cost-intensive.

It is the object of the present invention to provide a method for manufacturing dental prostheses, a method for creating a data record and a computer-readable medium by which dental prostheses can be manufactured. Preferably this is accomplished according to the invention less expensively and at the same time with sufficiently high precision.

SUMMARY OF THE INVENTION

According to one embodiment, a dental prosthesis is manufactured by a rapid prototyping method. This can be done relatively quickly and inexpensively as material for the dental prosthesis is only used to the extent to which it is concretely required for a dental prosthesis. The thus manufactured dental prostheses are subsequently processed by a machining method, such as a milling method. Thereby, the desired precision of the dental prostheses can be achieved. The processing can be e.g. finishing where only slight modifications of the dental prosthesis are made, such as smoothing surfaces etc., but the dental prosthesis is essentially already finished.

It is, for example, in particular avoided in the process that a tool of a machining method (e.g. a cutter head for milling) is occupied for a relatively long time with removing material which is far away from the surface of the dental prosthesis, so that removal can be essentially restricted to fine machining, which, however, can be performed relatively quickly.

The rapid prototyping method can be a laser sintering method (as already described above), or else any other rapid prototyping method, such as for example stereolithography, laser generation, fused deposition modeling, laminated object modeling, 3D-printing, contour crafting or multi-jet modeling as well as a polyjet method.

Each of these methods is suited for manufacturing a dental prosthesis, so that it can be subsequently (re)worked by a machining method, such as a milling method.

In case of dental prostheses which are to be covered, a certain surface roughness in certain areas is absolutely desirable. For example porcelain covers or other covers can be attached to rough surfaces enduringly. Insofar, the rough surface produced with rapid prototyping can be advantageous.

In a milling method, a steel or, even better, a diamond milling cutter can be used. With diamond milling cutters, particularly precise and smooth surfaces can be made.

A method where in particular the area of a preparation line or the internal area of a dental prosthesis is (re)worked with the milling method is particularly advantageous. In particular in the area of the preparation line, a shape of the dental prosthesis as exact as possible is desired to thus achieve a good enclosure. On the exterior, reworking is as a rule rather not desired as here a rough surface can be advantageous, in particular for covering. If the dental prosthesis is not to be covered, reworking with a machining method (e.g. milling method) can be also performed externally.

Furthermore, a method where a referencing is generated with the rapid prototyping method is advantageous. This referencing can be used to position the dental prosthesis or a milling cutter for the milling procedure. That means, by means of the referencing, the position of the manufactured dental prosthesis can be identified and/or defined for the milling procedure.

It is furthermore advantageous to create a shell or frame with the rapid prototyping method where the dental prostheses are held, so that the dental prostheses can be transported and/or positioned together with the shell or frame, for example, for the machining method, such as the milling procedure.

With the machining method, in particular the worked areas are to be advantageously smoothed.

It is furthermore advantageous to form excess material at least in one predetermined area with the rapid prototyping method, and to subsequently rework this area, where the excess material is removed (at least partially).

It is furthermore advantageous if in those areas where no rework is to be performed, the produced shape that has been manufactured in the rapid prototyping method remains within predetermined surfaces or is e.g. partially spaced from the same. In particular, by a surface roughness typical of the rapid prototyping method, areas result which are spaced from a predetermined surface if the surface otherwise altogether remains within the predetermined surface. The predetermined surface can be, for example, the surface that is to be manufactured according to a predetermined data record.

In the method, dental prostheses can be made of very diverse materials. Thus, a dental prosthesis of plastics, glass-fiber reinforced plastics, or a glass-fiber reinforced copolyamide are suitable. A metal or metal alloy, such as for example cobalt, cobalt alloy, chromium cobalt alloy, titanium or titanium alloy, gold or a gold alloy are also suitable. Ceramics, such as zirconium ceramics (in particular yttrium-stabilized zirconium ceramics), or aluminum oxide are also suitable as material for the dental prosthesis.

Furthermore, an embodiment where a manufactured dental prosthesis is sintered after manufacture and before working is advantageous. Thereby, the shaping manufacturing process of the dental prosthesis can be completed and the exact desired shape can be manufactured. Distortion of the dental prosthesis by subsequent sintering is thus excluded. It is, however, also possible to first rework a dental prosthesis with a milling method and to subsequently subject it to dense sintering. This is in particular advantageous with respect to the wear of milling cutters which is comparably low in the working of not yet completely sintered materials.

Another embodiment of the invention is a method for creating a data record, wherein a starting data record is used to obtain an end data record, so that in at least one area of a dental prosthesis manufactured with the end data record, excess material is provided compared to a dental prosthesis manufactured with the starting data record. The excess material results from the comparison of the two data records or from two dental prostheses manufactured according to the respective data record. The manufacture of the two dental prostheses according to the two data records need not be part of the method but only serve for defining the excess material.

The area or areas where excess material is to be present can be automatically determined; for this, the shape data themselves, and also other information can be used in the starting data record. Alternatively, the information can also be entered by an operator.

In the starting data record, e.g. the area of a preparation line and/or the internal area can be stored, besides the actual shape data. The information saying which part of the shape or the shape data represents the preparation line and/or the internal area is thus already provided. However, the information can also be automatically identified by computer analysis or entered by an operator.

Several end data records can also be further processed to form a production data record. Here, a data record is created with which a work piece can be produced where several dental prostheses are connected with connecting means, such as webs, one or several frames, one or several shells, etc.

One or several end data records as well as one production data record can serve for the manufacture of the dental prostheses with a corresponding rapid prototyping method. The thus prepared dental prostheses and/or the thus prepared work piece can be subsequently worked with a machining method, in particular with a milling method.

Another embodiment of the invention is a computer-readable medium comprising instructions performing one of the methods described above or below when they are read into a computer.

The manufacture of dental prostheses can be performed with two different computer-based manufacturing processes which are performed one after another. The manufacture can be furthermore performed batch-wise (lot-wise). That means, first a higher number of dental prostheses is manufactured with the first computer-based method, and subsequently (after completion of the first method for all dental prostheses manufactured thereby) they are worked with the second computer-based method. More than 50, 100, 150, 200 or 250 dental prostheses can be made in one batch.

The dental prostheses can be inlays, overlays, onlays, small caps, crowns, primary crowns, secondary crowns, bridges, shells, dentures (false teeth), abutments, implants, etc.

BRIEF DESCRIPTION OF THE DRAWINGS

Preferred embodiments of the method are to be illustrated with reference to the enclosed figures, wherein.

DETAILED DESCRIPTION OF THE INVENTION

Figure 1A:
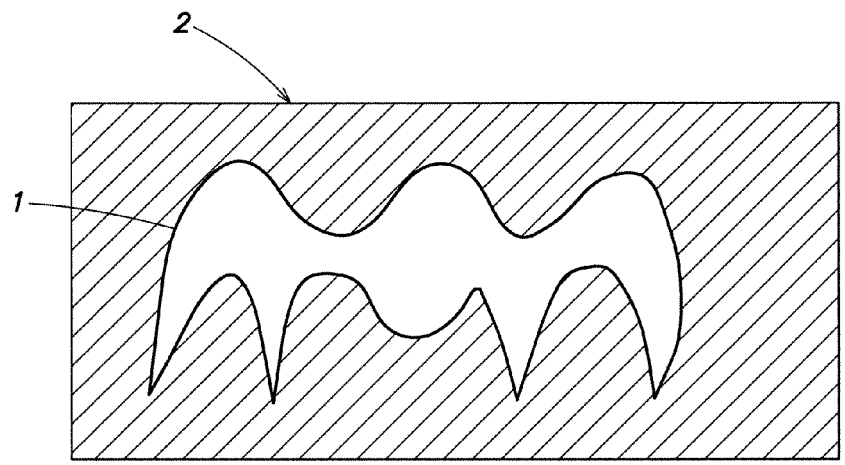
FIG. 1: shows a conventional manufacture of dental prostheses.

In FIG. 1a, a blank 2 from which a dental prosthesis 1 can be milled out is shown. For this, the complete shaded area of material has to be removed, which is relatively time consuming. With this milling method, it furthermore has to be taken into consideration that the portion of blank 2 which is not used for the dental prosthesis 1 is machined, that means it cannot be directly reused.

Figure 1B:
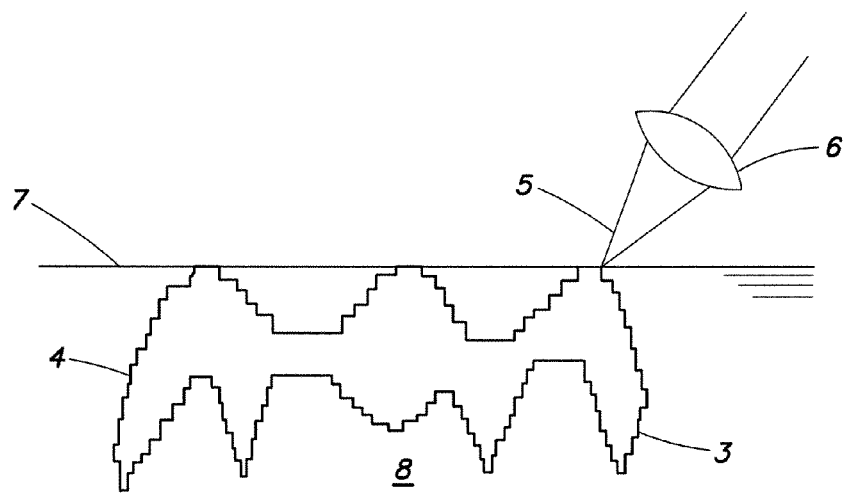

In FIG. 1b, an example of a rapid prototyping method is shown, in this case laser sintering. A powdery or liquid material is provided in area 8 which has been applied in layers, for example with a slider and locally melted (or otherwise modified) with a focused (see reference numeral 6) laser beam 5, so that it is subsequently solidified after cooling (or the like). The surface of the powder is marked with reference numeral 7.

In the section in FIG. 1b, the dental prosthesis 3 has a relatively high surface roughness 4. This is the result of the application of the material 8 to be solidified in layers and of the local solidification. This always results in step-like surfaces.

Figure 2:
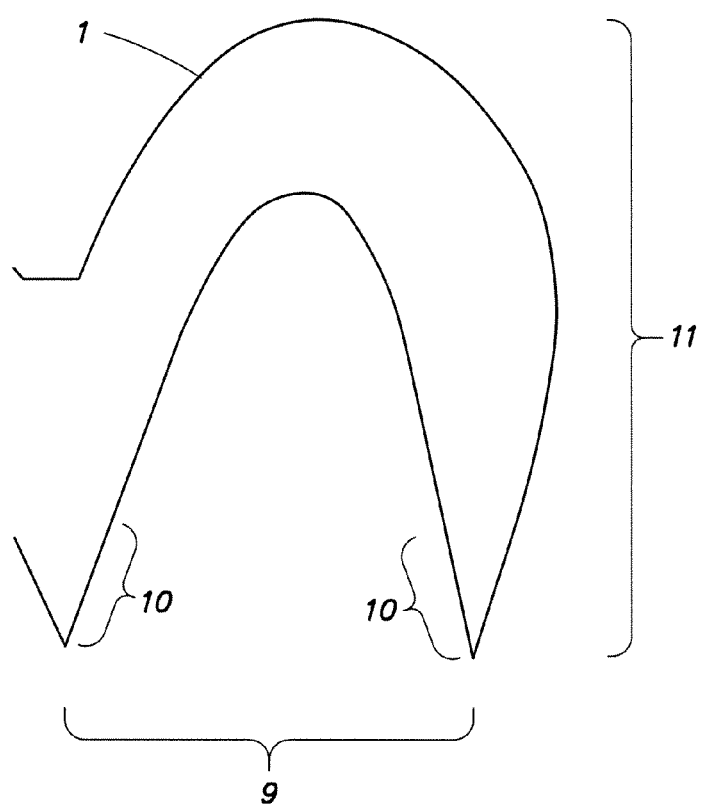
FIG. 2: shows certain typical areas of dental prostheses.

In FIG. 2, an enlarged section of a dental prosthesis 1 is shown, here a portion of a bridge which is to be placed onto a polished tooth or implant support. The area which comes into contact with the polished tooth or the implant support is the internal area 9. A portion of this internal area 9 is the area of the preparation line 10, that means the area which has to be worked particularly precisely in order to seal well the internal area 9 of the dental prosthesis 1 from the outside. This is important to avoid penetration of bacteria or other tooth-destroying substances.

The external area is marked with reference numeral 11. On the external area, covers or facings can be applied, for example of porcelain or the like. The external sides 11 can, however, also remain without facing.

Figure 3A:
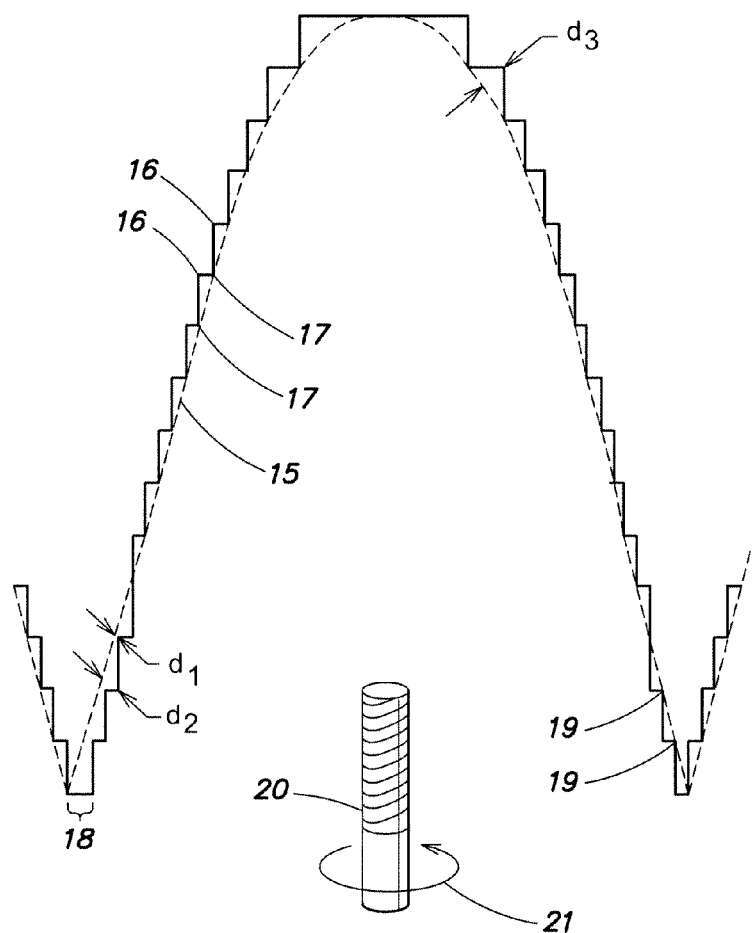
FIG. 3: shows the shape of dental prostheses according to one embodiment of the invention.

In FIG. 3a, an internal side of a dental prosthesis, manufactured according to an embodiment of the invention with a rapid prototyping method, is shown in section. In the upper portion of the internal side, the manufactured shape remains within the dashed line 15. Line 15 shows the shape which would optimally match with the polished tooth or implant support. This shape can be, for example, be specified by a corresponding data record. In the areas 17 of the step-like surface of the dental prosthesis, the surface of the prosthesis is situated on this line 15. In the corners 16, the surface is spaced apart from line 15. Here, for example a distance $d_3$ is provided.

In the areas of the preparation line 10 (see FIG. 2), the surface of the manufactured dental prosthesis may also be spaced apart from the line 15, here projecting over the line 15 to the outside. The concave corners (see distance $d_1$) as well as the convex corners (distance $d_2$) are situated outside the limiting surface 15, and comprise excess material 18.

On the right side of the preparation line of FIG. 3a, the corners 19 are situated on line 15 coming from the outside, however, excess material is provided in the areas between the corners 19.

The excess material 18 can be removed with a milling cutter 20. In FIG. 3a, an example of a milling cutter is schematically shown (see arrow of rotation 21) which is a triaxial milling machine (see 3D arrows marked as reference numeral 23). However, 3+1, 4 or 5-axial milling machines can also be provided.

Figure 3B:
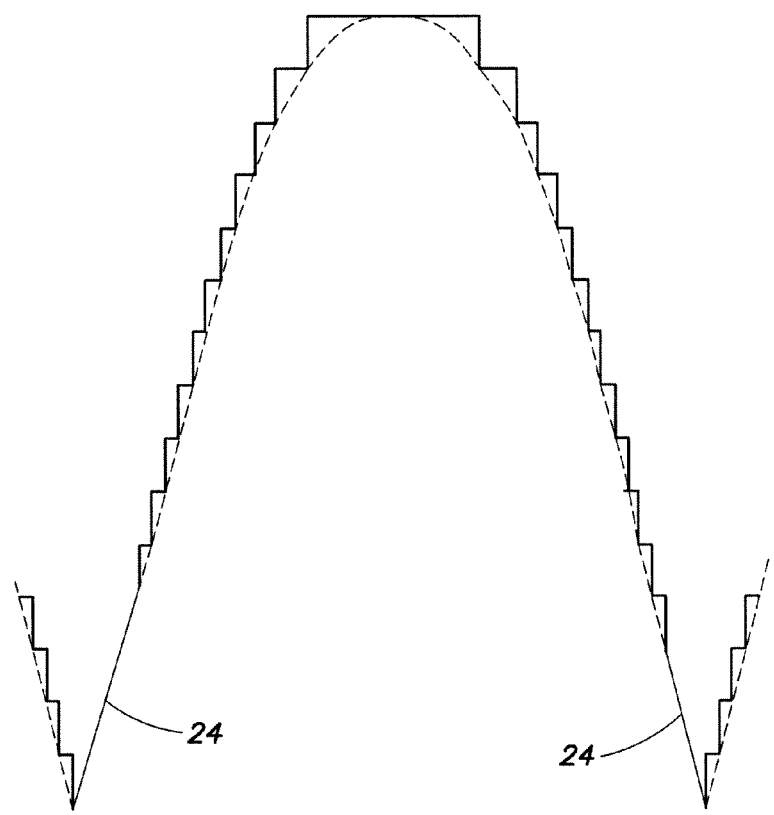

The result of a (re)working of the area of the preparation line 10 is shown in FIG. 3b. Here, excess material 18 is removed creating smooth surfaces 24 which are situated preferably as exactly as possible on the desired line 15 (dashed line).

While FIG. 3 shows a case where excess material exists only in the area of the preparation line 10 (see FIG. 2), there also is the possibility of providing the complete internal side 9 (see FIG. 2) with excess material and to subsequently rework it with the machining method. Thus, this area, which provides good support of the dental prosthesis and should have the desired shape preferably as exactly as possible, can be exactly made.

The outer side of the dental prosthesis 1 not represented in FIGS. 3a and 3b (or only indicated at the bottom) is step-like, as it is shown for example in FIG. 1b. This rough surface is well-suited for being subsequently covered.

According to one embodiment of the invention, it is also possible to rework the external side 11 or a portion thereof with the milling method. Excess material may be provided on the complete external side or a portion of the external side of the prototype prosthesis, some or all of which is then removed, e.g., by milling.

Even if the complete surface of the dental prosthesis which has been manufactured with the rapid prototyping method is reworked with the milling procedure, the milling procedure is relatively quick as it is normally sufficient to once pass over the surface with the milling cutter. A removal of volume material as it is, for example, necessary for forming the cavity of the cavity in the area of the internal side 9, can be omitted here. Thus, the milling working can be relatively quickly performed. This in general applies to any machining method. Furthermore, here relatively little material is machined, so that the manufacturing costs remain low.

In FIG. 3a, a starting data record 15 is shown (represented by the dashed line 15). The starting record has been modified such that in the area of the preparation line 10, excess material 18 is formed. The dental prosthesis that would have been manufactured with the starting data record 15 would not comprise such excess material.

The area of the preparation line, the internal area or any other area where excess material is to be arranged can be automatically identified and/or determined. Thus, e.g. the shape data 15 shown in FIG. 3a can be evaluated to identify the corresponding areas. Moreover, apart from the actual shape data, other data can also be provided in a data record by which the areas which are to be provided with excess material are marked. Thus, e.g. the area of a preparation line or the internal area can be marked and this information can be utilized for providing excess material in this area.

Figure 4:
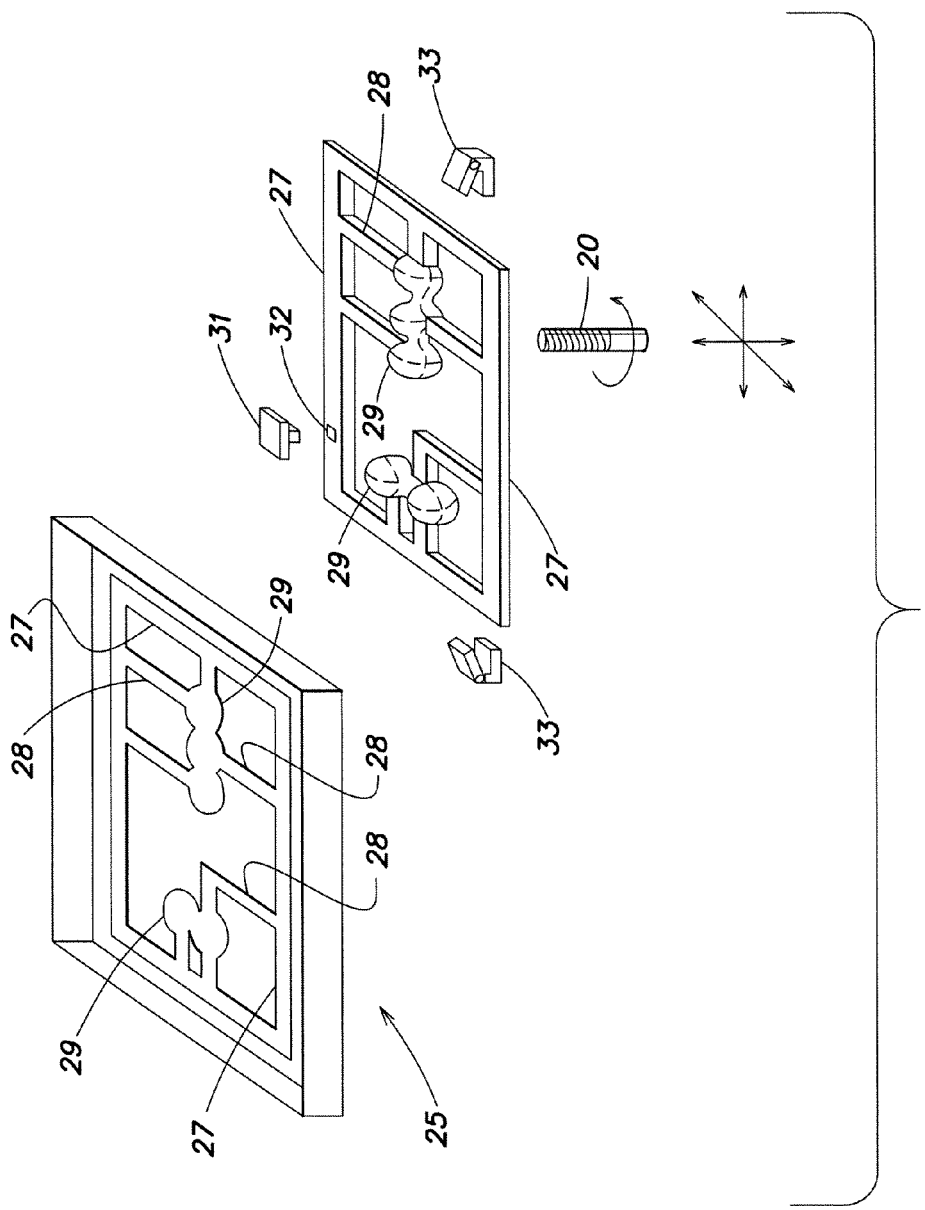
FIG. 4: shows a schematic representation of the manufacturing process according to one embodiment of the invention.

In FIG. 4, reference numeral 25 schematically represents one embodiment of a rapid prototyping device. It is shown in a condition where the manufactured work piece can be seen in a section and subsequently has to be finished at the top. Liquid or powdery material which is locally modified to thus produce a solidified structure is provided in a reservoir. In FIG. 4, a frame 27 from which webs 28 extend to dental prostheses 29 can be seen. The webs 28 can also be connected to each other without a frame 27 being provided. Furthermore, the dental prostheses 29 can also be arranged such that they are directly held by a frame 27 without webs. However, the variant shown in FIG. 4 is preferred, where there is a frame 27 from which webs extend and hold the dental prostheses 29. By way of example, two dental prostheses are shown, on the left hand a dental prosthesis 29 with two elements and on the right hand one with three elements. Several webs 28 extend to each dental prosthesis 29 to stably hold the dental prostheses 29. This is advantageous for working with a machining method.

For performing the rapid prototyping method according to one embodiment, a data record is used in which, apart from the data for the dental prostheses, also data for connecting means (webs, frames, etc.) are included. Such a data record can be created before the beginning of the rapid prototyping method from one or several end data records.

After the performance of the rapid prototyping method, the dental prostheses 29 can be completely removed at the frame 27. While in FIG. 4 two dental prostheses 29 are shown, the method is in particular advantageous for 50, 100, 150, 200, 250 or even more dental prostheses can be produced together. By the connection of the dental prostheses 29 with a frame 27, thus even more than 50, more than 100, 150, 200, 250 or more dental prostheses can be together produced and then removed from the rapid prototyping device. Furthermore, all dental prostheses can be together transferred to a milling device as one work piece (see right of FIG. 4).

In the right of FIG. 4, the work piece finished with the rapid prototyping method is shown. It comprises the frame 27 with the webs 28 which extend to the now completely shaped dental prostheses 29. The dental prostheses 29 held by the webs 28 can be correspondingly reworked with a milling cutter 20 (in the bottom of FIG. 4 schematically indicated), as explained above. Other machining methods than milling are also possible.

It is advantageous to form a referencing 32 with which the position of the dental prostheses 29 can be determined for the milling procedure. The geometrical relation between the dental prostheses 29 and the referencing 32 are known from the manufacturing data with which the rapid prototyping method is performed. This known relation can be utilized for determining, from the defined positioning of the referencing 32, the position of the dental prostheses 29. For referencing, any of various shapes, such as pyramids, cuboids, rectangles, triangles, hemispheres or combinations thereof can be employed. Any characteristic shape suited for defining or identifying the position of the work piece is suited for this. Referencing can be given by a projecting part and/or an indentation (see FIG. 4). In FIG. 4, for example, an element 31 of the machine for performing a machining method is shown which can be included in the referencing 32 or on which the referencing 32 can be guided, so that the position of the frame 27 or of the dental prostheses 29 is clearly defined.

As it is now possible to position the dental prostheses in a well-defined manner by referencing, the dental prostheses can also be first positioned in an undefined manner, then, however, the position can be determined by means of the referencing. Then, a milling cutter or a corresponding device of a machine for a machining method can correspondingly adjust the position of a correspondingly machining device, e.g. a cutter head.

For example, optically detectable shapes or marks can be provided, such as for example hemispheres in a certain geometry or the like, which can be optically easily detected, to then draw a conclusion on the position of the dental prostheses 29 after the detection of the referencing.

In FIG. 4, clamping jaws 33 with which the frame 27 for the milling procedure can be held are also schematically shown. The frame 27 can also be inserted into a correspondingly prepared supporting frame and subsequently fixed in this position. This is advantageous for the desired stability during the milling process. More than two, three, four or five means for supporting and/or fixing/defining the position of a work piece can also be provided.

After the treatment with the milling procedure, the individual dental prostheses are separated from the webs by breaking them out or detaching them. For this purpose, in the rapid prototyping method or milling (or any other machining method), corresponding break-off areas can be provided at the transitions between web or frame and the dental prosthesis.

Figure 5:
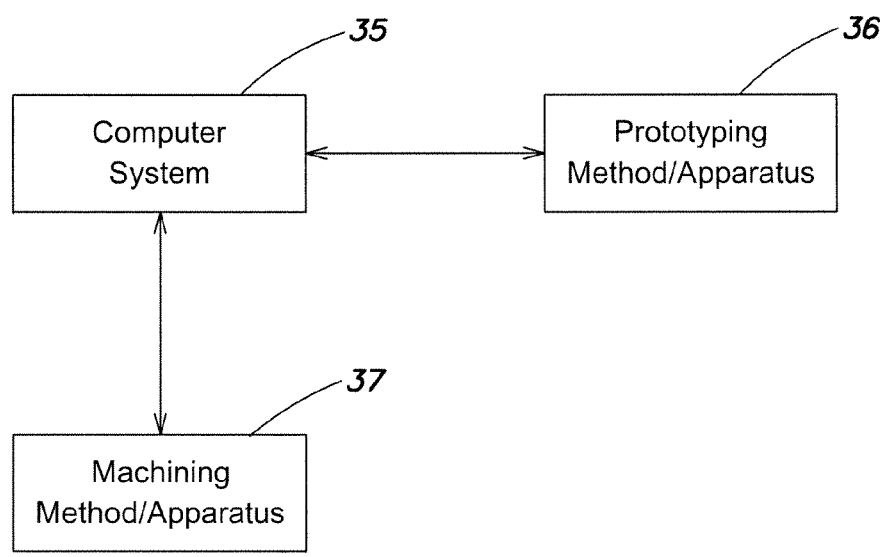
FIG. 5: shows a schematic representation of a computer system for implementing the prototyping and/or manufacturing according to one embodiment of the invention.

For performing the methods, according to various embodiments of the invention, correspondingly adapted devices can be provided, such as a combined rapid prototyping device with a means for a machining method, such as a milling device or correspondingly equipped computers, e.g. with the mentioned computer-readable media. FIG. 5 is a schematic of a computer 35 (e.g., processor and memory) for implementing the instructions on the computer-readable medium to perform the various methods of the invention as described herein, including the prototyping method 36 and/or the machining method 37.

The invention claimed is:

1. Method for creating a data record on a computer which can be used for a rapid prototyping method for manufacturing a dental prosthesis comprising:

obtaining an end data record from a starting data record, so that in at least one area of a dental prosthesis manufactured with the end data record, excess material is provided compared to a dental prosthesis manufactured with the starting data record, subsequently manufacturing the dental prosthesis with a rapid prototyping method with the end data record, wherein the manufactured dental prosthesis is subsequently worked with a machining method, in the area which is provided with the excess material.

2. Method according to claim 1, wherein the area where excess material is provided is automatically identified or predetermined by an operator or read out from specific information in the starting data record.

3. Method according to claim 1 or 2, wherein the excess material is provided in an area of a preparation line and/or in an area of an internal side of the dental prosthesis.

4. Method according to claim 1, wherein several starting data records of various dental prostheses are changed to become end data records, and the several end data records are summarized to become one production data record for manufacturing several dental prostheses.

5. Method according to claim 1, wherein several starting data records of various dental prostheses are changed to become end data records, and the several end data records are summarized to become one production data record for manufacturing several dental prostheses.

6. Method according to claim 1, wherein several dental prostheses are manufactured and connecting means are provided which connect the dental prostheses with each other.

7. Computer-readable medium having stored thereon instructions which perform, when loaded into a computer, the method steps according to claim 1.

8. Method according to claim 1, wherein a plurality of dental prostheses are manufactured at the same time.

* * * * *

UNITED STATES PATENT AND TRADEMARK OFFICE
CERTIFICATE OF CORRECTION

PATENT NO.         : 8,021,154 B2
APPLICATION NO.    : 12/056863
DATED              : September 20, 2011
INVENTOR(S)        : Holzner et al.

It is certified that error appears in the above-identified patent and that said Letters Patent is hereby corrected as shown below:

Title Page, Item (73) ASSIGNEE:

"Straumann Holding AG, Basel (CH)" should be --Institut Straumann AG, Basel (CH)--

Signed and Sealed this
Twenty-second Day of November, 2011

David J. Kappos
*Director of the United States Patent and Trademark Office*